United States Patent
Bush et al.

(10) Patent No.: US 12,130,350 B2
(45) Date of Patent: Oct. 29, 2024

(54) IMAGING AN OBJECT SUBJECTED TO A CYCLIC MOTION

(71) Applicant: Siemens Healthcare GmbH, Erlangen (DE)

(72) Inventors: Michael Bush, Brooklyn, NY (US); Thomas Benkert, Neunkirchen am Brand (DE); Thomas Vahle, Nüremberg (DE); Vibhas S. Deshpande, Austin, TX (US)

(73) Assignee: Siemens Healthineers AG, Forchheim (DE)

( * ) Notice: Subject to any disclaimer, the term of this patent is extended or adjusted under 35 U.S.C. 154(b) by 94 days.

(21) Appl. No.: 18/081,906

(22) Filed: Dec. 15, 2022

(65) Prior Publication Data

US 2023/0194642 A1    Jun. 22, 2023

(30) Foreign Application Priority Data

Dec. 17, 2021    (EP) .................................... 21215728

(51) Int. Cl.
*G01R 33/565* (2006.01)
*G01R 33/56* (2006.01)

(52) U.S. Cl.
CPC ... *G01R 33/56509* (2013.01); *G01R 33/5608* (2013.01)

(58) Field of Classification Search
CPC .......... G01R 33/56509; G01R 33/5608; G01R 33/5673; G01R 33/567; G01R 33/56308; A61B 5/055; A61B 5/721; A61B 6/032; A61B 6/486; A61B 6/5288; A61B 6/541; A61B 6/545; A61B 6/5264; A61B 6/527
See application file for complete search history.

(56) References Cited

U.S. PATENT DOCUMENTS

| | | | |
|---|---|---|---|
| 2016/0135718 A1* | 5/2016 | Covitch ................. | A61B 6/541 702/19 |
| 2017/0046832 A1* | 2/2017 | Hofmann ............... | A61B 6/032 |
| 2018/0289281 A1 | 10/2018 | Chaptinel et al. | |
| 2021/0181282 A1 | 6/2021 | Deller et al. | |

OTHER PUBLICATIONS

Motaal, Abdallah G., Nils Noorman, Wolter L. De Graaf, Luc J. Florack, Klaas Nicolay, and Gustav J. Strijkers. "Accelerated self-gated UTE MRI of the murine heart." In Medical Imaging 2014: Biomedical Applications in Molecular,. Structural, and Functional Imaging, vol. 9038, pp. 8-15. SPIE, 2014.

* cited by examiner

*Primary Examiner* — G. M. A Hyder
(74) *Attorney, Agent, or Firm* — Lempia Summerfield Katz LLC

(57) ABSTRACT

For imaging an object subject to a cyclic motion, two or more imaging repetitions are carried out. Each of the imaging repetitions includes a sequence of equally spaced imaging events, wherein each imaging event has an event number, which corresponds to a respective predefined imaging parameter. A cycle duration of the cyclic motion is determined, a number of events per cycle is determined based on the cycle duration and a shift number is determined at least in part randomly. For a first imaging repetition, a starting number is determined depending on the number of events per cycle and the shift number. The first imaging repetition is carried out, wherein the respective sequence is started with an imaging event, whose event number is given by the starting number.

20 Claims, 6 Drawing Sheets

IMAGING AN OBJECT SUBJECTED TO A CYCLIC MOTION

RELATED APPLICATION

This application claims the benefit of European Application EP 21215728.3, filed on Dec. 17, 2021, which is hereby incorporated by reference in its entirety.

FIELD

The present embodiments relate to a method for imaging an object, which is subject to a cyclic motion, wherein a predefined total number of two or more consecutive imaging repetitions is carried out by using an imaging modality. A duration of each imaging repetition is given by a predefined repetition time. Each of the two or more imaging repetitions are a sequence of equally spaced imaging events. Each imaging event has an event number, which corresponds to a respective predefined imaging parameter. The embodiments further relate to an imaging system for imaging an object, which is subject to a cyclic motion and to a computer program product or non-transitory computer readable medium.

BACKGROUND

When imaging an object, for example for medical purposes, the object may be subject to a cyclic motion. In case the object is a human or animal, the cyclic motion may for example correspond to a cardiac motion or a respiratory motion of the object.

An imaging procedure may include two or more consecutive imaging repetitions, each of them including a sequence of imaging events. The imaging events are labeled by event numbers, which correspond to a predefined imaging parameter. The different repetitions may for example be used for averaging purposes or for gathering data for different device settings, et cetera.

Such situations may for example occur in the context of magnetic resonance imaging, MRI, but also for camera-based imaging procedures, ultrasonic imaging, computer tomography, et cetera.

MRI systems use a strong external magnetic field to align nuclear spins of an object under examination and excite them to precess about the corresponding alignment by applying an excitation RF pulse. The precession or the transition of the spins from this excited state to a state with lower energy, respectively, generates an alternating electromagnetic field in response, which can be detected via receiving antennas as an MR signal.

With the aid of magnetic gradient fields, a position encoding can be impressed on the signals, which subsequently allows the received signal to be assigned to a volume element of the object under investigation. The received signal can then be analyzed, for example to provide an image representation of the object under examination.

In case of an MRI procedure, the different repetitions may for example correspond to different scans through the k-space and the different event numbers may correspond to different slices.

For reconstructing an image, data acquired during different repetitions but for the same or similar event numbers may be combined. Therefore, the influence of the cyclic motion may lead to motion artifacts and consequently to a reduced image quality.

SUMMARY AND DETAILED DESCRIPTION

It is an object to reduce the influence of a cyclic motion of an object to be imaged for imaging procedures containing two or more imaging repetitions, each imaging repetition including a sequence of imaging events.

This objective is achieved by the respective subject matter of the independent claims. Further implementations and preferred embodiments are subject matter of the dependent claims.

Artifacts may result from an unwanted partial synchronization of the sequences of imaging events with the cyclic motion. Therefore, a controlled dephasing is introduced. To this end, a repetition is started with an imaging event, whose event number is determined based on the maximum number of imaging events that fits into a cycle of the cyclic motion and based on a shift number, which is determined at least in part randomly.

According to an aspect, a method for imaging an object, which is subject to a cyclic motion, is provided. A predefined total number of two or more consecutive imaging repetitions is carried out by using an imaging modality of an imaging system, wherein a duration of each imaging repetition is given by, in particular is equal to, a predefined repetition time. Each of the two or more imaging repetitions includes a sequence of equally spaced, in particular equally spaced in temporal terms, imaging events. Each imaging event has an event number, which corresponds to a respective predefined imaging parameter, in particular a respective predefined value for the imaging parameter. A cycle duration of the cyclic motion is determined, in particular by a computing unit (computer) of the imaging system. A maximum number of events per cycle is determined, in particular by the computing unit, based on the cycle duration and based on the repetition time and based on a predefined event spacing time. A shift number is determined at least in part randomly, in particular by the computing unit. For a first imaging repetition of the two or more imaging repetitions, a starting number is determined, in particular by the computing unit, depending on the maximum number of events per cycle and depending on the shift number. The first imaging repetition is carried out, wherein the respective sequence of the first imaging repetition is started with an imaging event of the sequence of the first imaging repetition, whose event number is given by the starting number.

Here and in the following, a quantity denoted as number, for example a starting number or the shift number, is an integer number, if not stated otherwise.

The object is subject to the cyclic motion, which means that the object or a part of the object carries out the subject motion or is mechanically coupled to a further object, which carries out the cyclic motion. For example, in case the object is a human or animal or a body part of the human or animal, the cyclic motion may correspond to a respiratory or cardiac motion or may be caused by the respiratory and/or the cardiac motion. For example, in case the brain of the animal or human is examined, cerebrospinal fluid may undergo a cyclic motion, which is affected by the cardiac motion. Other inner organs may be affected by the cardiac motion and/or the respiratory motion of the lungs.

The imaging modality may be considered as a device or arrangement, which is capable of generating an image of the object or a part of the object. The imaging modality may be designed as or include a camera system, an X-ray-based system, such as a computer tomography system, an ultrasonic imaging system or an MRI system. The imaging modality may also combine different types of imaging.

Carrying out an imaging repetition may be understood such that the imaging modality carries out the respective sequence of imaging events of that repetition. During each of the imaging events, at least a part of the object is imaged according to the corresponding imaging parameter associated to the event number. In other words, during each of the imaging events, a respective dataset representing at least a part of the object is acquired. The dataset may represent the part of the object directly as an image or as another set of data in a position space. However, the dataset may also represent the object or part of the object in a k-space or in hybrid space, in particular if the imaging modality is an MRI modality.

In particular, one or more images representing the object may be reconstructed, in particular by the computing unit, depending on the datasets of the imaging events of the first repetition, in particular depending on the datasets of the imaging events of all of the two or more imaging repetitions.

In terms of the imaging parameters, each repetition of the two or more repetitions includes the same set event numbers and corresponding imaging events. For example, if the event numbers are a set of integer numbers running from 1 to N, wherein N is denoted as the number of events per sequence, each imaging repetition includes all imaging events with the numbers 1 to N. Also, the ordering of the imaging events may be the same for all repetitions. However, the starting numbers that is the event numbers of the initial imaging events may be different for different repetitions, in particular are different for all repetitions. For example, the sequence of one imaging repetition may run from 1 to N, while the sequence of another imaging repetition runs from j to N and then from N to j−1, wherein 1<j<N. In other words, the sequences of different imaging repetitions may correspond to each other except for a cyclic permutation of the event numbers.

The number of events per sequence N is at least 2, preferably at least 3. For example, the number of events per sequence N may be 10 to 100 depending on the details of the imaging procedure.

The value of the imaging parameter is uniquely associated to the corresponding event number. In other words, each repetition and each sequence of imaging events is carried out according to the same set of values for the imaging parameter. The imaging parameter may for example define a position and/or orientation of the part of the object to imaged, such as a slice along the excitation direction in case of an MRI, a camera orientation or a shape, position and/or orientation of an ultrasonic focus.

However, apart from the imaging parameter, the imaging may be carried out according to one or more further parameters. These are not necessarily the same for different imaging repetitions. For example, considering a diffusion weighted MRI imaging procedure, different b-values may be used for different repetitions. Alternatively, or in addition, different k-space trajectories for the same slice may be followed for different repetitions. For example, in case of an X-ray-based imaging procedure or a camera-based imaging procedure, different exposure times may be used for different repetitions.

For a given sequence of imaging events, the imaging events are equally spaced. That means for each successive pair of imaging events, the time between them is the same constant predefined event spacing time. In particular, this holds for all sequences of all repetitions. Consequently, the repetition time is given by the number of events per sequence N times the event spacing time. In other words, for a defined event spacing time, the repetition time is equivalent to the number of events per sequence N.

The first imaging repetition is not necessarily an initial imaging repetition of the two or more consecutive imaging repetitions. In other words, one or more imaging repetitions of the two or more consecutive imaging repetitions may be carried out prior to the first imaging repetition.

The cyclic motion may for example be monitored by a motion sensor system of the imaging system. For example, an amplitude of the cyclic motion may be measured or determined based on measurements of the motion sensor system as a function of time. Based on the measurements of the motion sensor system, in particular based on the monitored cyclic motion, the computing unit may determine the cycle duration. The cycle duration may correspond to a single period of the cyclic motion or, in other words, may be the inverse of the frequency of the cyclic motion.

However, the cycle duration may also be an integer multiple of the inverse frequency of the cyclic motion. In particular, the cycle duration may be chosen such that the cycle duration is greater than the repetition time. For example, the cycle duration may be chosen as short as possible while still being greater than the repetition time. In this way, it may be ensured that the repetition time is always at least as long as the cycle duration.

The maximum number of events per cycle corresponds to the maximum number of events, which may in principle be carried out during the cycle duration, and is therefore, in general, greater than the number of events per sequence. The maximum number of events per cycle may be computed as the cycle duration divided by the event spacing time.

The difference between the maximum number of events per cycle and the number of events per sequence may be denoted as number of additional events, which may be computed as the difference between the cycle duration and the repetition time divided by the event spacing time.

In other words, computing the number of additional events is equivalent to computing maximum number of events per cycle.

The shift number is determined at least in part randomly. This may be understood such that the shift number is not necessarily determined in a completely random or quasi random manner but determining the shift number may also include deterministic or rule-based steps. However, when determining the shift number, at least one random or quasi random step is to be carried out. For example, a subset of integer numbers may be determined in a deterministic manner, for example depending on the number of additional events, and the shift number may be selected in a random manner or randomly from the subset of integer numbers. In this way, it may be achieved that the shift number is, on the one hand, random to a certain degree and, on the other hand, lies in a certain desired range.

By determining the shift number at least in part randomly, also the starting number is determined at least in part randomly as a consequence. Therefore, it may be avoided that there is an unwanted synchronization between the cyclic motion and a periodicity given by the two or more repetitions and the corresponding sequences. By taking into account the maximum number of events per cycle or the number of additional events, respectively, as well as the randomly determined shift number, the dephasing becomes controllable since the maximum number of events per cycle is obtainable in a fully deterministic manner. Therefore, the maximum number of events per cycle or the additional number of events, respectively, may provide a starting point for controllably dephasing the imaging repetitions with respect to the cyclic motion based on the shift number.

It is understood that, as described for the first imaging repetition, the corresponding method acts may analogously be carried out for further imaging repetitions of the two or more imaging repetitions, for example for all imaging repetitions or for all but one of the imaging repetitions, namely for example for all but an initial imaging repetition. For the initial imaging repetition, the starting number may for example be predefined, for example may be equal to 1. Then for all other imaging repetitions, a respective shift number may be determined at least in part randomly to obtain a corresponding starting number.

Therein, the cycle duration may be determined once for all of the repetitions and the corresponding maximum number of events per cycle may be computed depending on the determined cycle duration. However, the cycle duration may also be dynamically adapted according to the monitored cyclic motion such that, during the course of carrying out the two or more imaging repetitions, the cycle duration change and therefore also the maximum number of events per cycle may change dynamically.

Due to the controlled dephasing, it is avoided that all imaging events according to a certain event number are carried out during the same or similar states or phases of the cyclic motion. Therein, the state or phase of the cyclic motion may for example be given by a corresponding value range of the amplitude of the cyclic motion. In this way, it is achieved that, for a given motion state or for a given range of amplitudes of the cyclic motion, respectively, datasets for all the event numbers are captured. Therefore, when reconstructing the image based on all the datasets, for example by binning the datasets according to the different motion states or amplitude ranges, the probability to have artifacts due to missing event numbers at a given motion state is decreased.

For example, respiratory motion may significantly degrade the quality of free breathing MRI examinations. Respiratory binning of image data into discrete motion states or motion amplitude bins without employing the invention may result in a suboptimal filling of motion bins and therefore lead to artifacts due to interpolation and registration errors. For example, all imaging repetitions for a particular slice may only be acquired in an end-inspiration state. After binning data to the end-expiratory state, there would be no information for this particular slice in this particular motion state.

According to several implementations of the method, a preceding imaging repetition of the two or more imaging repetitions is carried out prior to the first imaging repetition. In particular, the first imaging repetition is carried out directly after the preceding imaging repetition.

According to several implementations, the amplitude of the cyclic motion is monitored at least while the preceding imaging repetition is carried out and the cycle duration is estimated, in particular by the computing unit, based on the monitored amplitude, in particular the amplitude monitored while the preceding imaging repetition is carried out.

The amplitude of the cyclic motion is monitored, in particular, by the motion sensor system. The motion sensor system may for example include a respiratory belt, one or more cameras monitoring a motion of one or more markers attached to the object, a pilot tone sensor, et cetera.

In such implementations, the cycle duration is for example determined immediately before the first imaging repetition is carried out. Therefore, the probability that the actual cycle duration during the first imaging repetition is different from the determined cycle duration is reduced. Consequently, the reliability of the maximum number of events per cycle determined based on the cycle duration is increased.

The preceding imaging repetition may be started with an imaging event, whose starting number is a predefined number, for example is equal to 1. Alternatively, the starting number for the preceding imaging repetition may be determined in an analog manner as described for the first imaging repetition.

According to several implementations, a second imaging repetition of the two or more imaging repetitions is carried out after the first imaging repetition, in particular directly after the first imaging repetition.

The second imaging repetition is carried out such that the respective sequence of the second imaging repetition is started with an imaging event, whose event number is for example determined analogously to the event number of the first imaging repetition, for example based on the cycle duration of the cyclic motion monitored during the preceding imaging repetition or during the first imaging repetition.

In particular, the explanations with respect to the first imaging repetition and the second imaging repetition may hold analogously for all other imaging repetitions of the two or more imaging repetitions.

According to several implementations, a preliminary starting number is determined depending on the difference between the maximum number of events per cycle and the number of events per sequence N or, in other words depending on the number of additional events. The preliminary starting number is shifted according to the shift number to determining the starting number for the sequence of the first imaging repetition.

For example, the preliminary starting number may be given by (N−A+1), wherein A denotes the number of additional events. Therein, it is assumed that the event numbers are 1 to N.

Shifting the preliminary starting number according to the shift number may for example include a summation of the preliminary starting number and the shift number and a cyclic correction such that the shifted result is a number from 1 to N. In other words, the starting number may be given by (N−A+1+S) mod (N), wherein S denotes the shift number.

It is noted that the sequence of the first imaging repetition is not started with the preliminary starting number but with the starting number resulting from shifting the preliminary starting number according to the shift number. If the sequence would be started with the respective preliminary starting number for all the imaging repetitions, this would correspond to a completely synchronized situation between the cyclic motion and the periodicity given by the repetitions and consequently to the worst-case situation for the problem of artifacts described above. However, by computing the starting number based on the preliminary starting number with a shift, which is determined at least in part randomly, a fully controlled dephasing may be achieved.

According to several implementations, the shift number is determined as a random number or quasi random number.

According to several implementations, a set of equally spaced integer numbers, which are greater than 0 and smaller than the number of events per sequence N, is determined, in particular by the computing unit. The shift number is randomly selected from the set of equally spaced integer numbers or quasi randomly selected from the set of equally spaced integer numbers.

In particular, the set of equally spaced integer numbers includes R numbers, wherein R denotes the total number of repetitions of the two or more repetitions. Therefore, for each of the repetitions, a different shift number may be selected. Selecting the shift number randomly from the set of equally spaced random numbers may also be achieved by randomly reordering the set of equally spaced integer numbers and assigning them to the different repetitions in a predefined manner.

For example, the set of equally spaced integer numbers may be randomly reordered and the shift number for the first imaging repetition corresponds to a number of the randomly reordered set of equally spaced integer numbers, wherein the position of the number in the reordered set corresponds to the position of the first repetition in the sequence of two or more imaging repetitions.

By randomly selecting the shift number from the set of equally spaced integers, it is achieved that the difference between respective starting numbers of different imaging repetitions is maximized. The random reordering or, in other words the random selection of the shift number, ensures that the regular arrangement of the set of equally spaced integer numbers does not introduce another level of synchronization between the repetitions and the cyclic motion.

According to several implementations, the set of equally spaced numbers is determined such that a respective spacing between adjacent numbers is given by (N/R−1).

According to several implementations, the method is a method for MRI and the imaging modality includes an MRI scanner.

According to several implementations, during each of the imaging events, in particular during each of all imaging repetitions, a respective slice of the object is imaged, wherein the event number corresponds to a slice number and the imaging parameter is a corresponding slice position.

In particular, the slice position corresponds to a spatial position in a direction parallel to the direction of the homogenous basic magnetic field used for the MRI. In other words, selecting the imaging parameter according to the slice position, means that the respective parameter or parameters for exciting a slice at a corresponding slice position is tuned accordingly. Consequently, during each of the repetitions, the same slices are imaged.

According to several implementations, during each of the imaging events, in particular during each of the imaging events of all of the two or more imaging repetitions, a respective dataset representing a part of the object is generated. A plurality of adjacent amplitude intervals together ranging from a predetermined minimum amplitude of the cyclic motion to a predetermined maximum amplitude of the cyclic motion, is defined. Each of the generated datasets is associated to one of the plurality of amplitude intervals, in particular to exactly one of the plurality of amplitude intervals. One of the event numbers is selected and one of the plurality of amplitude intervals is selected. An image or a partial image is reconstructed based on a subset of the generated dataset, the subset containing only datasets corresponding to the selected event number and to the selected amplitude interval.

In other words, the datasets are binned according to the amplitude intervals by associating them to exactly one of the plurality of amplitude intervals. For each bin, a separate image or partial image may be reconstructed.

For example, different reconstructed images corresponding to the same selected event number but to different amplitude intervals may be combined to each other by registration or motion compensation techniques.

Since the starting number is determined as described, the probability that the subset is empty is reduced.

According to several implementations, the amplitude of the cyclic motion is monitored during all the two or more imaging repetitions. The generated datasets are associated to the plurality of amplitude intervals depending on the monitored amplitude.

In particular, the timing of the imaging events of the different repetitions and the correspondingly timing of the dataset generation with respect to the amplitude or the amplitude interval of the cyclic motion is known due to the monitoring of the amplitude of the cyclic motion. Furthermore, the amplitude intervals may also be defined based on the monitored amplitude by determining the maximum and minimum amplitude from the monitored data.

According to a further aspect, an imaging system for imaging an object, which is subject to a cyclic motion, is provided. The imaging system includes an imaging modality (scanner) and a control unit (controller), which is configured to control the imaging modality to carry out a predefined total number of two or more consecutive imaging repetitions. A duration of each imaging repetition is given by a predefined repetition time, and each of the two or more imaging repetitions includes a sequence of equally spaced imaging events, wherein each imaging event has an event number, which corresponds to a respective predefined imaging parameter. The imaging system includes a computing unit, which is configured to determine a cycle duration of the cyclic motion and to determine a shift number at least in part randomly. The computing unit is configured to determine a maximum number of events per cycle based on the cycle duration, the repetition time, and a predefined event spacing time. The computing unit is configured to determine, for a first imaging repetition of the two or more imaging repetitions, a starting number depending on the maximum number of events per cycle and depending on the shift number. The control unit is configured to control the imaging modality to carry out the first imaging repetition, wherein the respective sequence is started with an imaging event, whose event number is given by starting number.

The control unit and the computing unit may be implemented separate to each other. However, in other implementations, the computing unit and the control unit may be implemented as a common computing and control unit.

According to several implementations of the imaging system, the control unit is configured to control the imaging modality to carry out a preceding imaging repetition prior to the first imaging repetition. The imaging system includes a motion sensor system, which is configured to monitor an amplitude of the cyclic motion at least while the preceding imaging repetition is carried out. The computing unit is configured to determine the cycle duration based on the monitored amplitude.

For example, the motion sensor system may include a respiratory belt, a pilot tone sensor system and/or one or more cameras.

According to several implementations, the imaging modality includes an MRI scanner.

Further implementations of the imaging system follow directly from the various implementations of the method for imaging an object and vice versa. In particular, an imaging system is configured to or programmed to carry out a method or an imaging system carries out such a method.

According to a further aspect, a computer program including instructions stored on a non-transitory storage medium is provided. When the computer program or the instructions, respectively, are executed by an imaging system, in particular by the computing unit and/or the control unit of the imaging system, the instructions cause the imaging system to carry out a method for imaging an object.

According to a further aspect, a computer readable storage medium storing a computer program is provided.

The computer program and the computer readable storage medium may be considered as respective computer program products including the instructions.

If it is mentioned in the present disclosure that a component of the imaging system, in particular the computing unit or the control unit of the imaging system, is adapted, configured or designed to, et cetera, to perform or realize a certain function, to achieve a certain effect or to serve a certain purpose, this can be understood such that the component, beyond being usable or suitable for this function, effect or purpose in principle or theoretically, is concretely and actually capable of executing or realizing the function, achieving the effect or serving the purpose by a corresponding adaptation, programming, physical design, and so on.

A computing unit may in particular be understood as a data processing device, which includes processing circuitry. The computing unit can therefore in particular process data to perform computing operations. This may also include operations to perform indexed accesses to a data structure, for example a look-up table, LUT. The control unit of the imaging system may also be considered as a computing unit according to this understanding.

In particular, the computing unit may include one or more computers, one or more microcontrollers, and/or one or more integrated circuits, for example, one or more application-specific integrated circuits, ASIC, one or more field-programmable gate arrays, FPGA, and/or one or more systems on a chip, SoC. The computing unit may also include one or more processors, for example one or more microprocessors, one or more central processing units, CPU, one or more graphics processing units, GPU, and/or one or more signal processors, in particular one or more digital signal processors, DSP. The computing unit may also include a physical or a virtual cluster of computers or other of said units.

In various embodiments, the computing unit includes one or more hardware and/or software interfaces and/or one or more memory units (memories).

A memory unit may be implemented as a volatile data memory, for example a dynamic random access memory, DRAM, or a static random access memory, SRAM, or as a non-volatile data memory, for example a read-only memory, ROM, a programmable read-only memory, PROM, an erasable read-only memory, EPROM, an electrically erasable read-only memory, EEPROM, a flash memory or flash EEPROM, a ferroelectric random access memory, FRAM, a magnetoresistive random access memory, MRAM, or a phase-change random access memory, PCRAM.

BRIEF DESCRIPTION OF THE DRAWINGS

In the following, the embodiments will be explained in detail with reference to specific exemplary implementations and respective schematic drawings. In the drawings, identical or functionally identical elements may be denoted by the same reference signs. The description of identical or functionally identical elements is not necessarily repeated with respect to different figures.

In the figures.

DETAILED DESCRIPTION OF THE PREFERRED EMBODIMENTS

Figure 1:
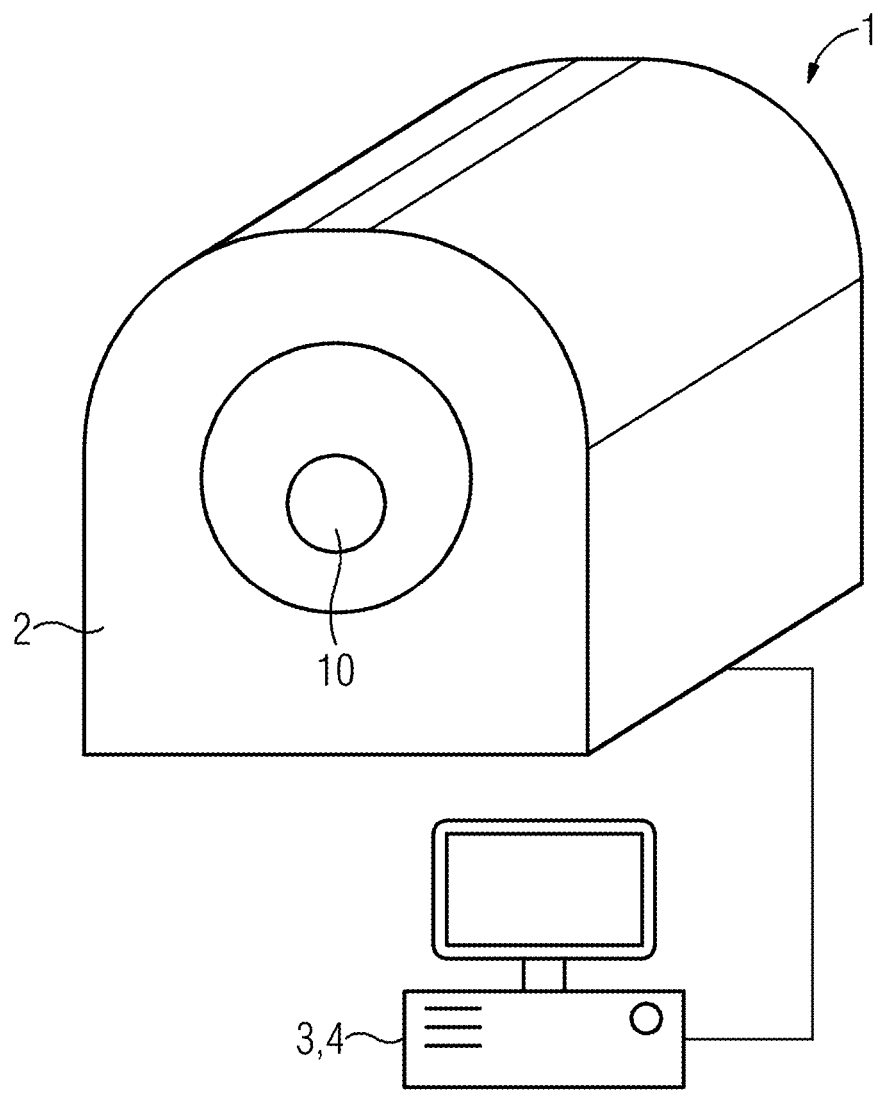
FIG. 1 shows schematically an exemplary implementation of an imaging system.

FIG. 1 shows schematically an imaging system 1, for imaging an object 10, which is subject to a cyclic motion. The imaging system includes an imaging modality (scanner) 2 and a control unit (controller) 3 as well as a computing unit (computer) 4.

For example, the imaging system 1 may be an MRI system and the imaging modality 2 may be an MRI scanner. The object 10 may be a human or animal, and the cyclic motion may for example be a respiratory motion of the object 10. However, it is emphasized, that the embodiment is not restricted to MRI systems nor is it restricted to a respiratory motion as cyclic motion.

Figure 3:
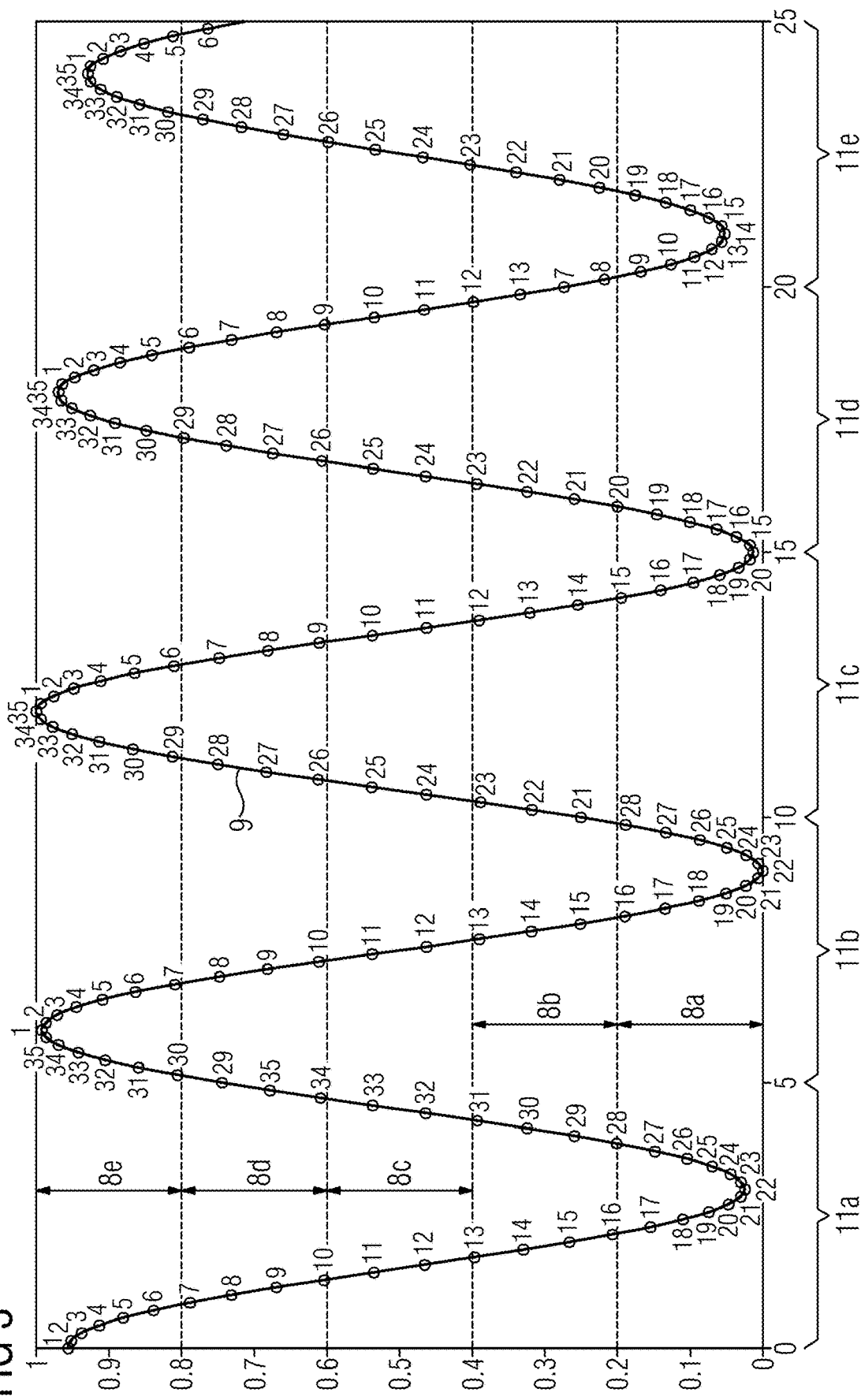
FIG. 3 shows schematically examples of a plurality of respiratory cycles and temporal positions of imaging events.
Figure 5:
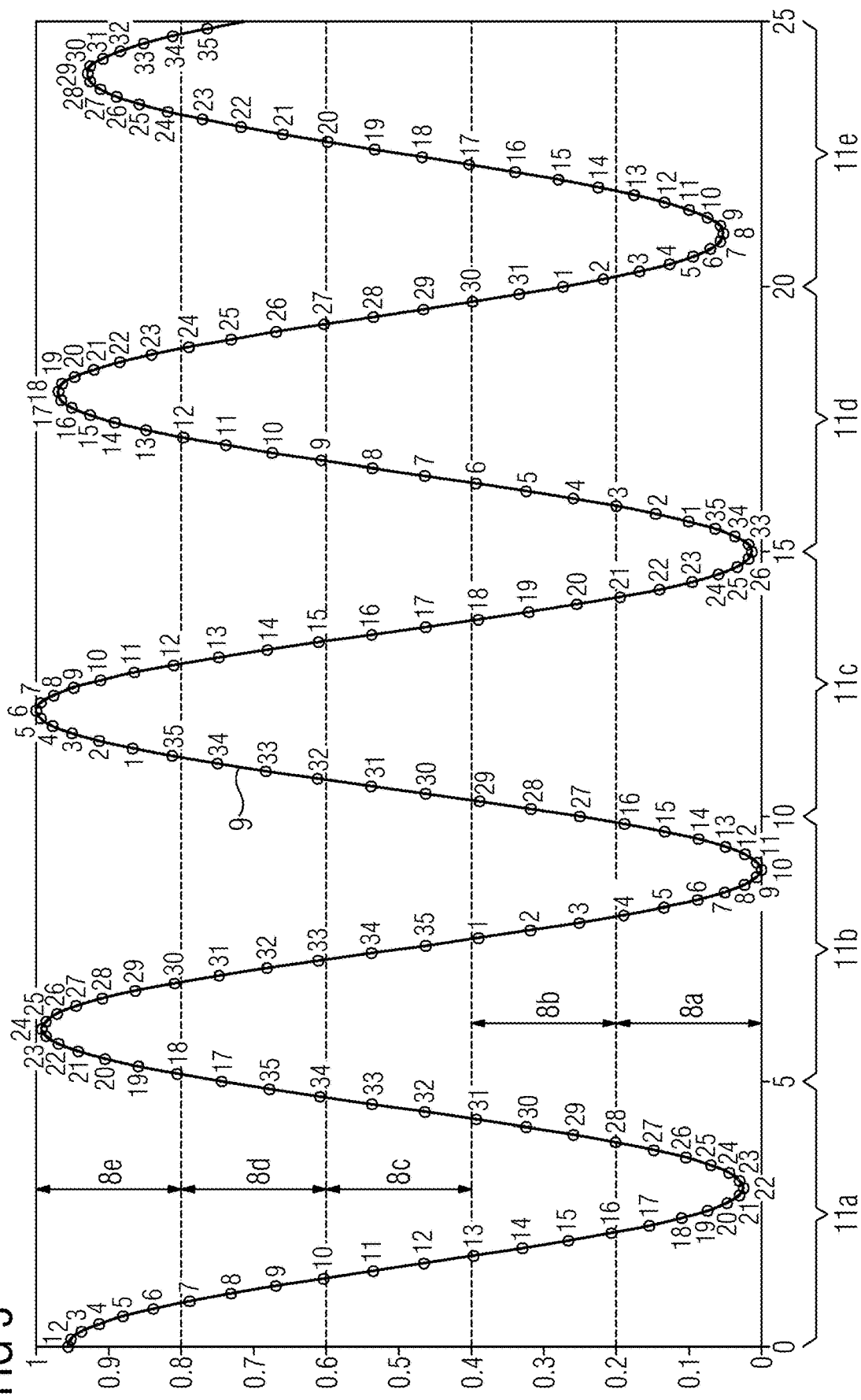
FIG. 5 shows schematically examples of a plurality of respiratory cycles and a timing of imaging events according to an exemplary implementation of a method.

The control unit 3 is configured to control the imaging modality 2 to carry out a plurality of consecutive imaging repetitions 11a, 11b, 11c, 11d, 11e (see FIG. 3 and FIG. 5). A duration of each imaging repetition is given by predefined repetition time and each of the imaging repetitions 11a, 11b, 11c, 11d, 11e includes a sequence of equally spaced imaging events, wherein each imaging event has an event number, which corresponds to a respective predefined imaging parameter.

In the non-limiting example of the MRI system as an imaging system 1, the different imaging events and the different imaging parameters may correspond to different slices to be imaged by the imaging modality 2. During each of the imaging events, a corresponding dataset representing the object 10 or a part of the object 10 is acquired.

Figure 2:
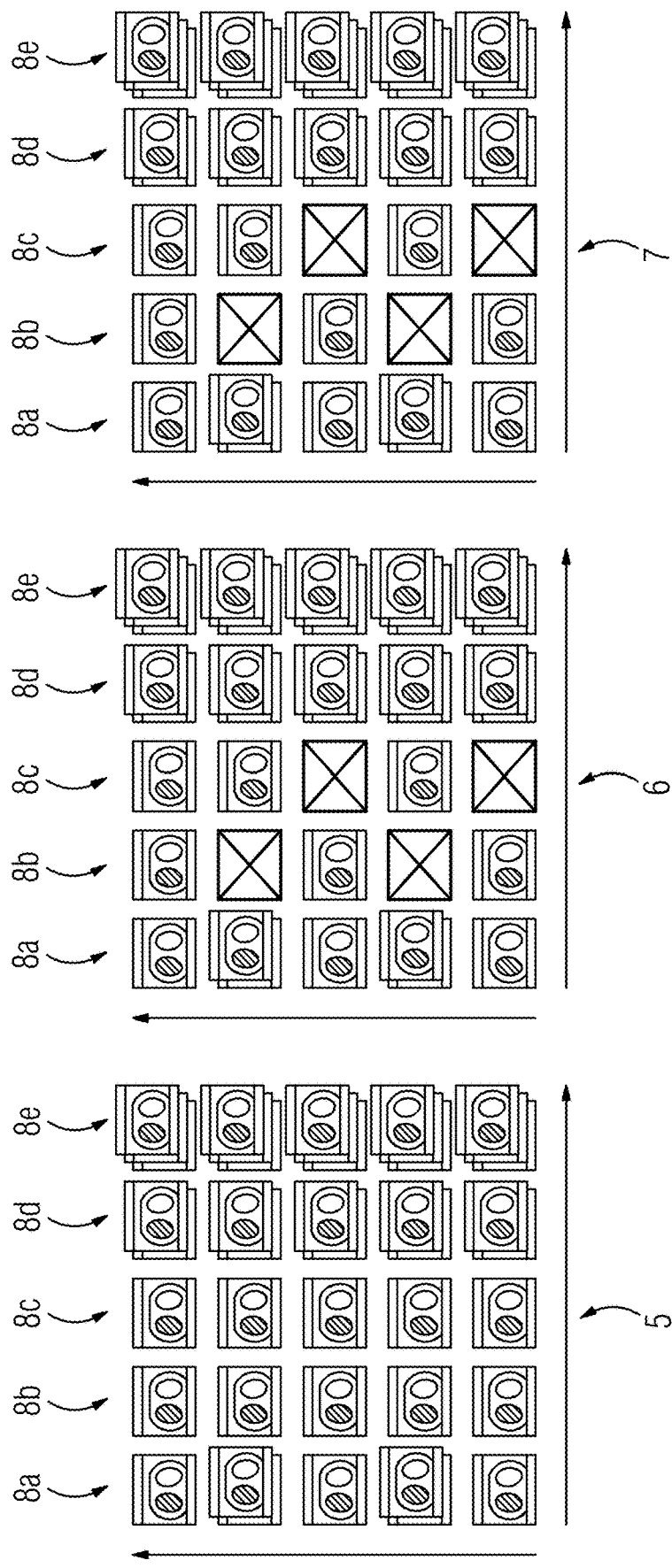
FIG. 2 shows schematically datasets generated according to an exemplary implementation of a method for imaging an object.

An example for the acquired datasets is shown schematically in FIG. 2. FIG. 2 shows three acquisitions 5, 6, 7, each acquisition 5, 6, 7 including a plurality of imaging repetitions. Considering for example the acquisition 5, five different bins corresponding to amplitude intervals 8a, 8b, 8c, 8d, 8e (see FIG. 3 and FIG. 5) are depicted on the horizontal axis and five different slice positions are depicted on the vertical axis. The datasets of the acquisition 5 are binned according to their respective amplitude intervals 8a, 8b, 8c, 8d, 8e such that for each amplitude interval 8a, 8b, 8c, 8d, 8e and each slice position, one or more respective datasets are obtained.

For a given slice position, the different datasets of different amplitude intervals 8a, 8b, 8c, 8d, 8e may be registered with respect to each other such that a corresponding image may be reconstructed for each slice. Alternatively, for each slice and for each amplitude interval, a separate image may be reconstructed.

In acquisition 6, a similar situation is shown. However, for some of the combinations of amplitude interval and slice position, in particular for the amplitude interval 8b and the amplitude interval 8c, no datasets have been acquired, which is depicted by respective crosses. The same holds analogously for a third acquisition 7.

For example, when carrying out a procedure for diffusion weighted MRI, the acquisitions 5, 6, 7 may correspond to different b-values.

The probability that empty bins occur for a given slice positions may be reduced. In particular, the computing unit 4 may determine a cycle duration of the cyclic motion, for example by a monitored amplitude of the cyclic motion, which is monitored by a motion sensor system (not shown) of the imaging system 1.

The computing unit 4 may determine a number of additional events in addition to the imaging events of a single imaging repetition 11a, 11b, 11c, 11d, 11e, which may be carried out during a cycle duration. The number of additional events is, in particular, determined based on the cycle duration, the repetition time and the predefined event spacing time between consecutive imaging events.

The computing unit 4 determines, for a given imaging repetition, a starting number depending on the number of additional events and depending on a shift number, which is determined at least in part randomly. The control unit 3 is configured to control the imaging modality 2 to carry out the respective imaging repetition such that the sequence of imaging events starts with the imaging event, whose event number is given by the starting number.

The procedure is illustrated in more detail with the respect to the exemplary representations of FIG. 3 to FIG. 6.

In FIG. 3, the monitored amplitude of the respiratory motion shown as a curve 9. The range of the amplitudes is distributed amongst the five adjacent amplitude intervals 8a, 8b, 8c, 8d, 8e. In the example of FIG. 3, five imaging repetitions 11a, 11b, 11c, 11d, 11e, each including 35 imaging events with event numbers from 1 to 35 are carried out.

As can be seen from FIG. 3, after the 35 imaging events of the first imaging repetition 11a are completed, the cycle of the respiratory motion curve 9 has not ended yet. The computing unit 4 may therefore compute, how many additional events may be carried out until the cycle of the respiratory motion is completed. In this case shown in FIG. 3, the number of additional events is seven. Therefore, seven events of the second imaging repetition 11b may be carried out during the remaining part of the cycle duration. For example, the computing unit 4 may determine a preliminary starting number for the second imaging repetition 11b such that the first imaging event with the event number 1 is carried out more or less exactly one cycle duration after the first imaging event of the first imaging repetition 11a. In the present example that means that the preliminary starting number of the second imaging repetition would be 29 as shown in FIG. 3. In this way, for each of the imaging repetitions 11a, 11b, 11c, 11d, 11e, a preliminary starting number may be determined.

However, the imaging repetitions 11a, 11b, 11c, 11d, 11e are not actually carried out with their sequences of imaging events starting with the preliminary starting number, since this would obviously result in a high degree of synchronization between the repetitions and the cyclic motion. Rather, the starting numbers for the individual imaging repetitions 11a, 11b, 11c, 11d, 11e are computed by the computing unit 4 by randomly shifting the preliminary starting numbers.

For example, the computing unit 4 may determine five shift numbers, which are equally spaced within the interval 1 to 35. In this case, the shift numbers could be determined for example to be 6, 12, 18, 24 and 30. The shift numbers are then randomly distributed or associated to the individual imaging repetitions 11a, 11b, 11c, 11d, 11e. In other words, the respective preliminary starting number is shifted by the corresponding randomly distributed shift number to obtain the actual starting number for the respective imaging repetition. The resulting distribution of imaging events is shown schematically in FIG. 5. In this case, the starting number of the first imaging repetition 11a is 1, the starting number of the second imaging repetition 11b is 17, the starting number of the third imaging repetition 11c is 27, the starting number of the fourth imaging repetition 11d is 32 and the starting number of the fifth imaging repetition 11e is 1.

In this way, a controlled dephasing or decorrelation of the respiratory motion and the repetitions is achieved.

Figure 4:
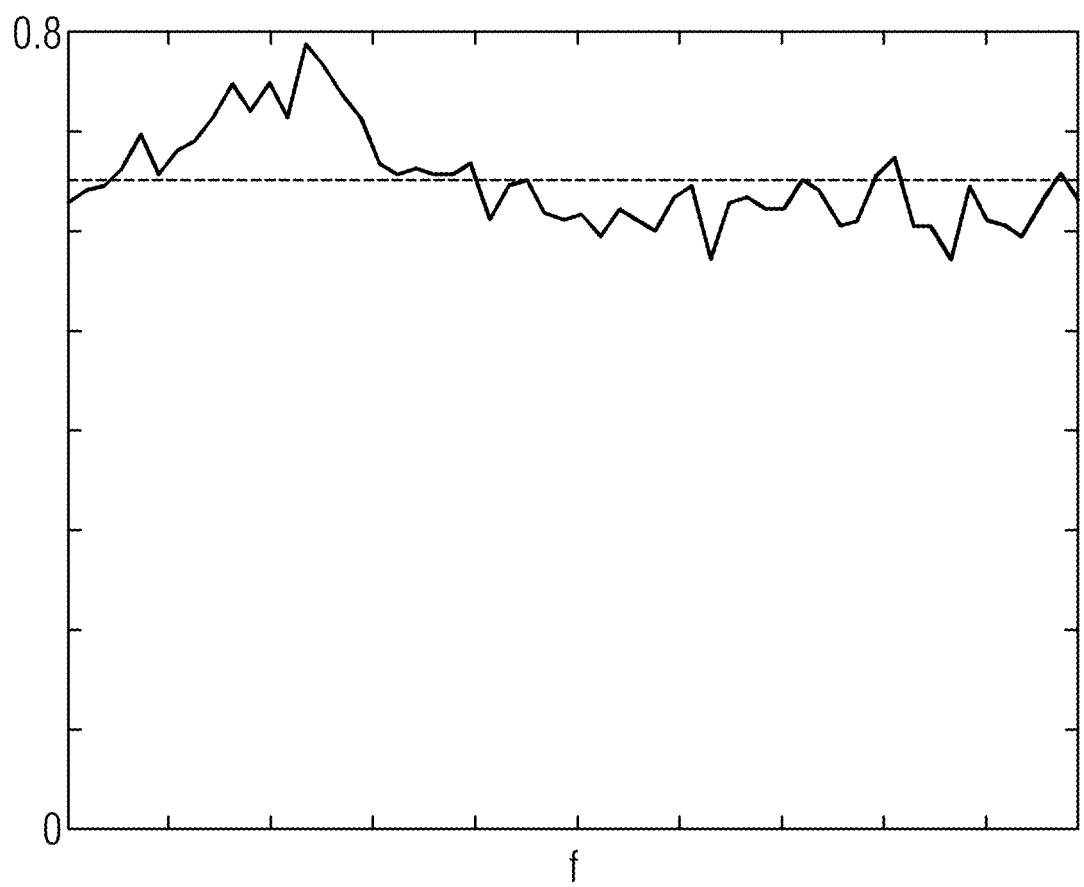
FIG. 4 shows schematically an example of a probability for missing datasets as a function of respiratory frequency.
Figure 6:
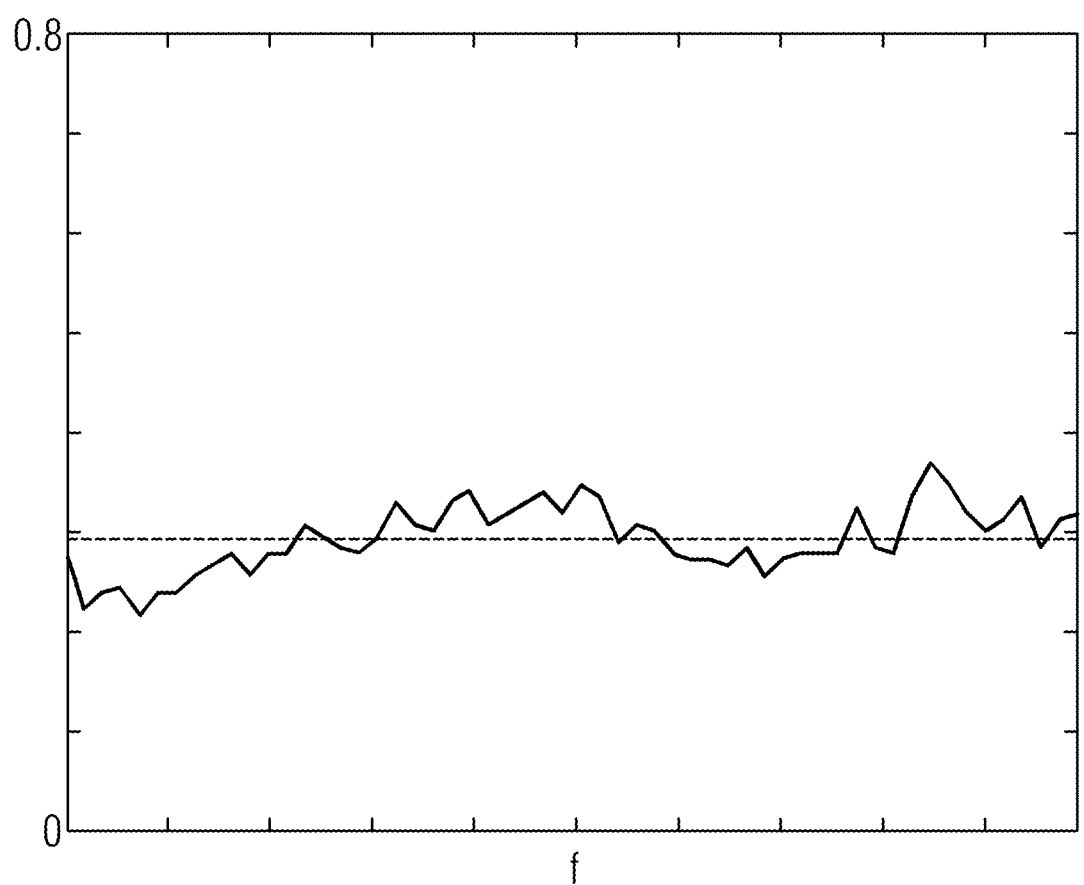
FIG. 6 shows schematically an example of a further probability for missing datasets as a function of the respiratory frequency.

The effect of the dephasing is shown in figures FIG. 4 and FIG. 6, respectively. FIG. 4 shows as a function of the respiratory frequency f, the fraction of empty bins in other words the fraction of combinations of slice position, and amplitude intervals 8a, 8b, 8c, 8d, 8e, for which no dataset is acquired. The dashed line represents the mean value. Therein, FIG. 4 corresponds to a situation where the preliminary starting number is used as a starting number or in other words the shift numbers are all 0. As can be seen, in this worst-case situation, the mean fraction of empty bins is approximately 0.65.

In contrast, FIG. 6 shows the fraction of empty bins as a function of f achieved when the repetitions are carried out as described with respect to the invention by shifting the preliminary starting numbers randomly. As can be seen, the mean value may be reduced to approximately 0.3.

Respiratory motion may significantly degrade the quality of free-breathing MRI examinations. Respiratory binning of image data into discrete motion states may been used to mitigate motion artifacts. The implementation avoids suboptimal filling of motion states and resultant artifacts due to interpolation and registration errors. For example, all repetitions for one particular image slice might only be acquired in end-inspiration. After binning data to the end-expiratory state, there would be no information for this particular slice in this particular motion state. This is illustrated for example in FIG. 2, as explained. The optimal solution would occur when all data acquired can be used to obtain one motion corrected image free of interpolation artifacts.

According to several implementations, the proposed technique starts from a situation where the acquisition loop of raw data is synchronized with the respiratory cycle based on the repetition time and the respiratory frequency. Then, a calculated shift can be applied to the data acquisition loop that ensures new image information is acquired within the current motion state. This reduces the amount of missing image information in each motion state regardless of the relationship between the respiratory cycle and repetition time.

There are many potential applications including free-breathing long-running imaging examination, such as 4D-MRI in radiation therapy, which requires reconstruction of different respiratory phases. These techniques perform at their best when image information is spread evenly over the motion states used in the final reconstruction.

Instead of relying only on retrospective binning, which is susceptible to missing data. In some implementations, the invention reduces the amount of missing data prospectively, which can also be combined with advanced retrospective binning techniques.

It is intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

The invention claimed is:

1. A method for imaging an object subject to a cyclic motion, wherein a predefined total number of two or more consecutive imaging repetitions is carried out by using an imaging modality, wherein a duration of each imaging repetition is given by a predefined repetition time, wherein each of the two or more imaging repetitions comprises a sequence of equally spaced imaging events, wherein each imaging event has an event number, which corresponds to a respective predefined imaging parameter, the method comprising:
  determining a cycle duration of the cyclic motion;
  determining a maximum number of events per cycle based on the cycle duration, the repetition time, and a predefined event spacing time;
  determining a shift number at least in part randomly;
  determining, for a first imaging repetition of the two or more imaging repetitions, a starting number depending on the maximum number of events per cycle and the shift number; and
  carrying out the first imaging repetition, wherein the respective sequence is started with an imaging event, whose event number is given by the starting number.

2. The method according to claim 1, wherein a preceding imaging repetition of the two or more imaging repetitions is carried out prior to the first imaging repetition; and/or a second imaging repetition of the two or more imaging repetitions is carried out after the first imaging repetition.

3. The method according to claim 2, wherein an amplitude of the cyclic motion is monitored at least while the preceding imaging repetition is carried out; and the cycle duration is estimated based on the monitored amplitude.

4. The method according to claim 1, wherein a preliminary starting number is determined depending on a difference between the maximum number of events per cycle and a number of events per sequence, and wherein the preliminary starting number is shifted according to the shift number to determine the starting number.

5. The method according to claim 1, wherein a set of equally spaced numbers, which are greater than zero and smaller than the number events per sequence, is determined, and the shift number is selected randomly from the set of equally spaced numbers.

6. The method according to claim 5, wherein the set of equally spaced numbers is determined such that a respective spacing is given by (N/R−1), wherein N denotes the number of events per sequence and R denotes the total number of the two or more repetitions.

7. The method according to claim 1, wherein carrying out the first imaging repetition comprises carrying out magnetic resonance imaging, MRI, and the imaging modality comprises an MRI scanner.

8. The method according to claim 7, wherein during each of the imaging events, a respective slice of the object is imaged, wherein the event number corresponds to a slice number and the imaging parameter is a corresponding slice position.

9. The method according to claim 1, wherein during each of the imaging events, a respective dataset representing a part of the object is generated, a plurality of adjacent amplitude intervals together ranging from a predetermined minimum amplitude of the cyclic motion to a predetermined maximum amplitude of the cyclic motion, is defined, each of the generated datasets is associated to one of the plurality of amplitude intervals, one of the event numbers is selected and one of the plurality of amplitude intervals is selected, and an image is reconstructed based on a subset of the generated datasets, the subset containing only datasets corresponding to the selected event number and to the selected amplitude interval.

10. The method according to claim 9, wherein the amplitude of the cyclic motion is monitored during the two or more imaging repetitions, and the generated datasets are associated to the plurality of amplitude intervals depending on the monitored amplitude.

11. The method according to claim 1, wherein the object is a human or an animal, and the cyclic motion corresponds to a respiratory motion or a cardiac motion of the human or animal.

12. An imaging system for imaging an object subject to a cyclic motion, wherein the imaging system comprises an imaging scanner and a controller, which is configured to control the imaging scanner to carry out a predefined total number of two or more consecutive imaging repetitions, wherein a duration of each imaging repetition is given by a predefined repetition time and wherein each of the two or more imaging repetitions comprises a sequence of equally spaced imaging events, wherein each imaging event has an event number, which corresponds to a respective predefined imaging parameter, the imaging system comprising:
  a computer configured to determine a cycle duration of the cyclic motion, determine a shift number at least in part randomly, determine a maximum number of events per cycle based on the cycle duration, the repetition time, and a pre-defined event spacing time, and determine, for a first imaging repetition of the two or more imaging repetitions, a starting number depending on the maximum number of events per cycle and depending on the shift number, and
  wherein the controller is configured to control the imaging scanner to carry out the first imaging repetition, wherein the respective sequence is started with an imaging event, whose event number is given by the starting number.

13. The imaging system according to claim 12, wherein the controller is configured to control the imaging scanner to carry out a preceding imaging repetition prior to the first imaging repetition; and
  further comprising a motion sensor system configured to monitor an amplitude of the cyclic motion at least while the preceding imaging repetition is carried out; and
  wherein the computer is configured to determine the cycle duration based on the monitored amplitude.

14. The imaging system according to claim 13, wherein the imaging scanner comprises an MRI scanner.

15. The imaging system according to claim 12, wherein the computer is configured to determine a set of equally spaced numbers, which are greater than zero and smaller than the number events per sequence and to select the shift number randomly from the set of equally spaced numbers.

16. The imaging system according to claim 12, wherein during each of the imaging events, a respective dataset represents a part of the object, a plurality of adjacent amplitude intervals together range from a predetermined minimum amplitude of the cyclic motion to a predetermined maximum amplitude of the cyclic motion, each of the generated datasets is associated to one of the plurality of amplitude intervals, wherein the computer is configured to select one of the event numbers and one of the plurality of amplitude intervals, and the imaging scanner is configured to reconstruct an image based on a subset of the generated datasets, the subset containing only datasets corresponding to the selected event number and to the selected amplitude interval.

17. A non-transitory computer readable storage medium comprising instructions, which, when executed by an imaging system, cause the imaging system (1) to:
    determine a cycle duration of cyclic motion;
    determine a shift number at least in part randomly;
    determine a maximum number of events per cycle based on the cycle duration, a repetition time, and a predefined event spacing time;
    determine, for a first imaging repetition of two or more imaging repetitions, a starting number depending on the maximum number of events per cycle and depending on the shift number; and
    control an imaging scanner to carry out the first imaging repetition, wherein the respective sequence is started with an imaging event, whose event number is given by the starting number.

18. The non-transitory computer readable storage medium of claim 17, wherein the instructions further comprise instructions to:
    control of the imaging scanner to carry out a preceding imaging repetition prior to the first imaging repetition; and
    monitor an amplitude of the cyclic motion at least while the preceding imaging repetition is carried out; and
    determine the cycle duration based on the monitored amplitude.

19. The non-transitory computer readable storage medium of claim 17, wherein the instructions further comprise instructions to determine a set of equally spaced numbers, which are greater than zero and smaller than the number events per sequence and to select the shift number randomly from the set of equally spaced numbers.

20. The non-transitory computer readable storage medium of claim 17, wherein, during each of the imaging events, a respective dataset represents a part of the object, a plurality of adjacent amplitude intervals together range from a predetermined minimum amplitude of the cyclic motion to a predetermined maximum amplitude of the cyclic motion, and each of the generated datasets is associated to one of the plurality of amplitude intervals, wherein the instruction further comprises instructions to select one of the event numbers and one of the plurality of amplitude intervals, and reconstruct an image based on a subset of the generated datasets, the subset containing only datasets corresponding to the selected event number and to the selected amplitude interval.

* * * * *